(12) United States Patent
Hung et al.

(10) Patent No.: US 8,148,683 B2
(45) Date of Patent: Apr. 3, 2012

(54) METHOD FOR CHARACTERIZING A MEMBRANE IN A WET CONDITION BY POSITRON ANNIHILATION SPECTROMETER AND SAMPLE HOLDER THEREOF

(75) Inventors: Wei-Song Hung, Chung-Li (TW);
Manuel De Guzman, Chung-Li (TW);
Shu-Hsien Huang, I-Lan (TW);
Kueir-Rarn Lee, Chung-Li (TW);
Yan-Ching Jean, Kansas City, MO (US); Juin-Yih Lai, Chung-Li (TW)

(73) Assignee: Chung Yuan Christian University, Tao-Yuan (TW)

(*) Notice: Subject to any disclaimer, the term of this patent is extended or adjusted under 35 U.S.C. 154(b) by 156 days.

(21) Appl. No.: 12/814,991

(22) Filed: Jun. 14, 2010

(65) Prior Publication Data
US 2011/0284743 A1    Nov. 24, 2011

(30) Foreign Application Priority Data
May 21, 2010 (TW) ............................. 99116352 A

(51) Int. Cl.
*G01N 23/00* (2006.01)
(52) U.S. Cl. ............... 250/307; 250/309; 250/440.11
(58) Field of Classification Search ......... 250/306–443.1
See application file for complete search history.

(56) References Cited

U.S. PATENT DOCUMENTS

| | | | |
|---|---|---|---|
| 7,041,508 B2 * | 5/2006 | Smith | 436/104 |
| 7,230,242 B2 * | 6/2007 | Behar et al. | 250/310 |
| 7,421,885 B2 * | 9/2008 | Kitzhoffer et al. | 73/38 |
| 2004/0173745 A1 * | 9/2004 | Uedono et al. | 250/309 |
| 2006/0011831 A1 * | 1/2006 | Naik et al. | 250/308 |
| 2007/0145289 A1 * | 6/2007 | Chao et al. | 250/440.11 |
| 2008/0197070 A1 * | 8/2008 | Sirkar et al. | 210/500.27 |
| 2009/0218489 A1 * | 9/2009 | Akers et al. | 250/307 |

OTHER PUBLICATIONS

Wei-Song, Manuel De Guzman, Shu-Hsien Huang, Kueir-Rarn Lee, Yan-Ching Jean, Juin-Yih Lai, Characterizating free volumes and layer structures in asymmetric thin-film polymeric membranes in the wet condition using the variable monoenergy slow positron beam, pp. 1-37, ACS Paragon Plus Environment, Macromolecules Journal article, Scholar one Manuscript Central, manucript IS ma-2010-00559u.R1.

* cited by examiner

*Primary Examiner* — Jack Berman
*Assistant Examiner* — David E Smith
(74) *Attorney, Agent, or Firm* — WPAT., P.C.; Justin King

(57) ABSTRACT

The present invention discloses a method for characterizing a membrane in a wet condition using a positron annihilation spectrometer and a sample holder thereof. Positron annihilation lifetime spectroscopy (PALS) has been know to be an invaluable tool for investigating local free-volume hole properties in various materials. Accompanying with the method and sample holder disclosed by the invention, PAS and PALS can measure the properties of various materials, such as free volume and layer structures both in the dry and wet states.

20 Claims, 4 Drawing Sheets

METHOD FOR CHARACTERIZING A MEMBRANE IN A WET CONDITION BY POSITRON ANNIHILATION SPECTROMETER AND SAMPLE HOLDER THEREOF

BACKGROUND OF THE INVENTION

1. Field of the Invention

The present invention is generally related to a method for characterizing a membrane by a positron annihilation spectrometer and the sample holder thereof, and more particularly to a method for characterizing a membrane in a wet condition by a positron annihilation spectrometer and the sample holder thereof.

2. Description of the Prior Art

Pervaporation is a membrane separation process that combines the technologies of permeation and evaporation and has attracted a great deal of research to deal with its application in dehydrating aqueous alcohol solutions. High performance pervaporation membranes are specifically based on two criteria: the increase of permeation flux and the enhancement of selectivity. In this respect, asymmetric thin-film composite (TFC) membranes consisting of a thin dense top layer and a porous supporting layer are a feasible alternative. Since a thin selective skin layer has lower mass transfer resistance, the permeation flux can be enhanced during the pervaporation process. Nevertheless, the swelling problem inherently persists no matter which method is applied to modify membrane materials. Since pervaporation membranes are always in direct contact with the feed solution whose components are to be separated, the membranes inevitably experience a certain degree of swelling. There is a strong interaction between the feed solution components and the pervaporation membrane. To better understand such an interaction, it is essential to characterize the swelling behavior of a membrane.

However, the measurement of the extent of the swelling behavior in thin-film composite membranes encounters technical problems because most conventional instruments available are basically designed for application to free-standing membranes. With the advent of positron annihilation spectroscopy (PAS), the method for determining the swelling behavior of TFC membranes has been dramatically improved. However, characterizations of composite membranes are still done in their dry state. Therefore, a method for characterizing a membrane in a wet condition by a positron annihilation spectrometer is very important for the industries.

SUMMARY OF THE INVENTION

In light of the above background, in order to fulfill the industrial requirements, the invention provides a method for characterizing a membrane in a wet condition by a positron annihilation spectrometer and the sample holder thereof. Positron annihilation lifetime spectroscopy has been known to be an invaluable tool to investigate local free-volume hole properties in various materials. By utilizing the method and the sample holder according to the invention, free volumes and layer structures of membranes in a wet condition can be measured and characterized.

One embodiment of the present invention is to provide a method for characterizing a membrane in a wet condition by a positron annihilation spectrometer. The method comprises the following steps. At first, a membrane to be characterized is provided where the membrane has a first surface and a second surface opposing to the first surface. A plasma polymerization procedure on the first surface of the membrane is performed to form a glass-like protective layer. The membrane formed with the glass-like protective layer is mounted on a sample holder to have the first surface of the membrane exposed and the second surface vacuum sealed in the sample holder. A liquid is injected into the sample holder through an inlet on the sample holder to have the liquid be in contact with the second surface of the membrane. After the inlet is sealed, the sample holder is placed into the vacuum chamber of the positron annihilation spectrometer. Finally, a positron beam impacts the glass-like protective layer to thereby characterize the membrane and obtain the characteristic(s) of the membrane. In the above, the glass-like protective layer has a property of vacuum sealing that the liquid can not permeate into the vacuum chamber through the glass-like protective layer.

Another embodiment of the present invention is to provide a sample holder suitable to be used in measuring the characteristic of a membrane in a wet condition by a positron annihilation spectrometer. The sample holder comprises a front plate and a back plate. The front plate has an opening and the back plate comprises a groove and an inlet where the inlet connects to the groove. The membrane has a first surface and a second surface opposing to the first surface and a glass-like protective layer is formed on the first surface. The membrane is clamped between the front plate and the back plate. The first surface of the membrane is in contact with the front plate and the glass-like protective layer is exposed toward outside of the sample holder through the opening of the front plate. The second surface of the membrane connects to the groove of the back plate. After gaps between the front plate and the membrane and between the membrane and the back plate are vacuum sealed, a liquid is injected into the groove and then the inlet is vacuum sealed so that the liquid is in contact with the second surface of the membrane to have the membrane in a wet condition.

According to the sample holder disclosed by the invention, the liquid is in contact with the membrane and sealed in the sample holder together with the membrane except that the glass-like protective layer deposited on the first surface of the membrane is exposed through the window (opening) of the front plate of the sample holder. Thus, the membrane in a wet condition can be placed into the vacuum system of the positron annihilation spectrometer without influencing the high vacuum environment of the vacuum system and at the same time can accept the impact of the positron beam so that the characteristics of the membrane in a wet condition can be measured by investigating the annihilation lifetime of ortho-positronium (o-Ps, a triplet bound state between a positron and an electron).

Another embodiment of the present invention is to further provide a sample holder suitable to be used in measuring the characteristics of at least one membrane in a wet condition by a positron annihilation spectrometer. The sample holder comprises a front plate and a back plate. The front plate has at least one opening and the back plate comprises at least one groove and at least one inlet where each groove corresponds to one inlet of the back plate and one opening of the front plate and the numbers of openings, grooves, inlets are the same. Each membrane has a first surface and a second surface opposing to the first surface and a glass-like protective layer is formed on the first surface of each membrane. Each membrane is clamped between the front plate and the back plate. The first surface of each membrane is in contact with the front plate and the glass-like protective layer is exposed toward outside of the sample holder through the corresponding opening of the front plate. The second surface of each membrane connects to the corresponding groove of the back plate. After gaps between the front plate and each membrane and between each membrane and the back plate are vacuum sealed, at least one liquid is injected into at least one groove to have the corresponding membrane in a wet condition and then the corresponding inlet is vacuum sealed.

According to the above sample holder disclosed by the invention, a plurality of membranes can be mounted on the sample holder simultaneously and various liquid can be separately injected to be in contact with different membranes. By providing the sample holder on a motion feedthrough, a plurality of sets, some of which may contain a membrane and a liquid and some of which may contain a membrane with no liquid, can be studied.

Other objectives and advantages of the invention can be further understood through the disclosed technical characteristics. Accompanying with the following figures, examples and claims, the above and other objectives and advantages of the invention will be described in details in the following.

DESCRIPTION OF THE PREFERRED EMBODIMENTS

Figure 1:
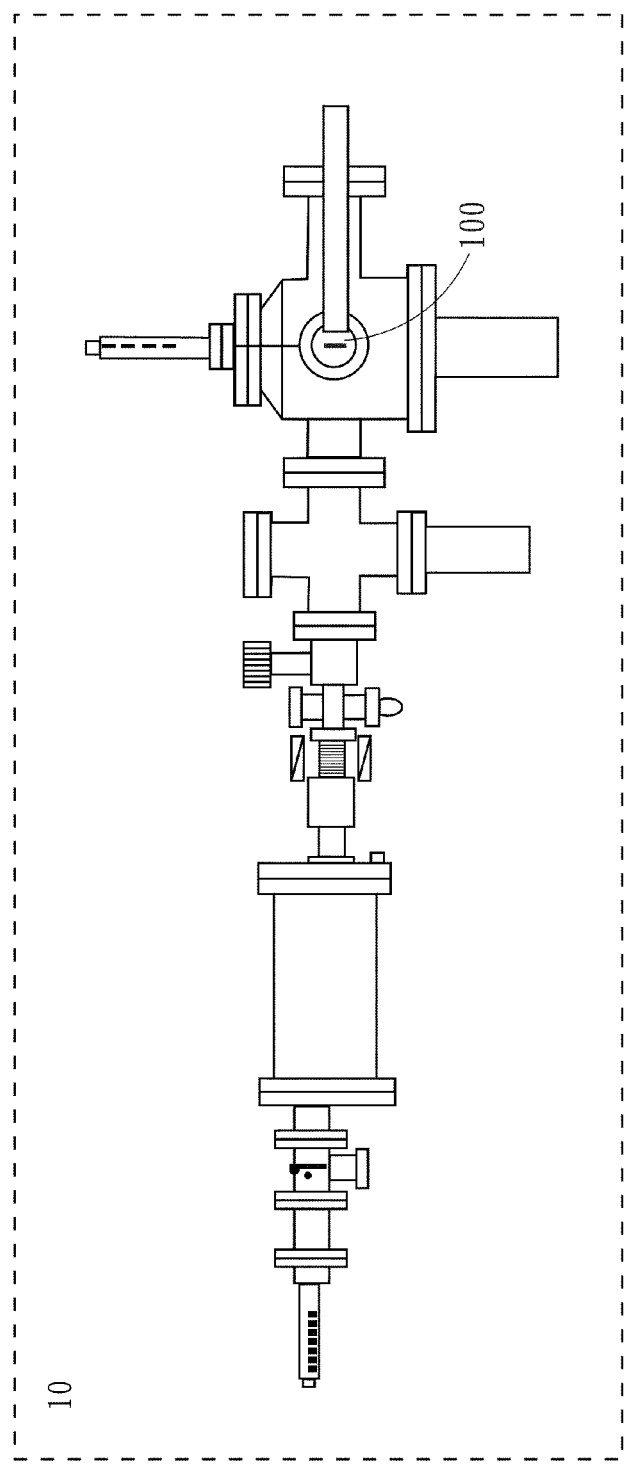
FIG. 1 shows a schematic diagram illustrating a positron annihilation spectrometer.

What is probed into the invention is a method for characterizing a membrane in a wet condition by a positron annihilation spectrometer and the sample holder thereof. Detail descriptions of the processes and elements will be provided in the following in order to make the invention thoroughly understood. Obviously, the application of the invention is not confined to specific details familiar to those who are skilled in the art. On the other hand, the common processes and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Characterizations of composite membranes are usually done by combining positron annihilation spectroscopy (PAS) and the variable monoenergy slow positron beam (VMSPB) technique but still in their dry state. The measurement result for the dry state exists the above mentioned problems that do not reflect the actual application condition. Thus, the present invention provides a new method to characterize a membrane in a wet condition.

Positron annihilation lifetime spectroscopy (PALS) is capable of investigating local free-volume hole properties in various materials. In the case of polymers and solutions, a sub-nano-order hole radius ranges from around 0.1 to 0.5 nm. Ortho-positronium (o-Ps, a triplet bound state between a positron and an electron) localized in a free-volume hole can be sensitively detected with PALS measurements. A good correlation between the observed "pick off" o-Ps annihilation lifetime and the cavity size has been rationalized based on a simple quantum mechanical model (referred to Tao, S. J. *J. Chem. Phys.* 1972, 56, p. 5499-5510 or Eldrup, M; Lightbody, D.; Sherwood, J. N. *Chem. Phys.* 1981, 63, p 51-58). A calibrated semi-empirical equation between the observed o-Ps lifetime and the mean free-volume hole size has been established. Thus, PALS is the only available technique at present that provides direct information about the size, concentration, and electronic nature of microscopic holes in polymers.

In addition, while the membrane is to be detected by a variable monoenergy slow positron beam (VMSPB), the membrane should maintain in a wet condition in order to obtain the representative depth profile of the multilayered structure of the membrane. Therefore, the invention provides a method for characterizing a membrane in a wet condition. The following will describe the method according to the invention together with PAS and VMSPB applicable to asymmetric membrane systems in the wet state.

In a first embodiment of the present invention, a method for characterizing a membrane in a wet condition by a positron annihilation spectrometer is disclosed. The method comprises the following steps. At first, a membrane to be characterized is provided where the membrane has a first surface and a second surface opposing to the first surface. A plasma polymerization procedure on the first surface of the membrane is performed to form a glass-like protective layer. The membrane formed with the glass-like protective layer is mounted on a sample holder to have the first surface of the membrane exposed toward the outside of the sample holder and the second surface vacuum sealed in the sample holder. A liquid is injected into the sample holder through an inlet on the sample holder to have the liquid be in contact with the second surface of the membrane. After the inlet is sealed, the sample holder is placed into the vacuum chamber of the positron annihilation spectrometer. Finally, a positron beam impacts the glass-like protective layer to thereby characterize the membrane and obtain the characteristic(s) of the membrane. In the above, the glass-like protective layer has a property of vacuum sealing that the liquid can not permeate into the vacuum chamber through the glass-like protective layer.

In the above method, the plasma polymerization procedure can be performed by using a plasma enhanced chemical vapor deposition method to form a glass-like protective layer comprising silicon, oxygen, carbon, and hydrogen on the first surface of the membrane. The glass-like protective layer is not limited to be formed by the plasma enhanced chemical vapor deposition method. In another embodiment, the glass-like protective layer can be a deposition layer comprising silicon, oxygen, carbon, and hydrogen and formed by any other method. In the above method, sealing the inlet can be performed by using a vacuum sealant to seal the inlet to prevent air from passing through the inlet. The characteristics of the membrane obtained from the method can be, for example, the free volumes or layer structure of the membrane. Besides, the thickness of the glass-like protective layer is 650 nm~5000 nm to have a property of vacuum sealing that the liquid can not permeate into the vacuum chamber through the glass-like protective layer and preferably around 700 nm~1500 nm. If the glass-like protective layer were too thick, it is unfavorable for the positron beam to impact the membrane during measurement. On the contrary, if the glass-like protective layer were too thin, the glass-like protective layer may not be able to prevent air from permeating into the vacuum chamber through the glass-like protective layer.

The sample holder used in the above method comprises a front plate and a back plate. The front plate has an opening and the back plate comprises a groove and an inlet where the inlet connects to the groove. The membrane has a first surface and a second surface opposing to the first surface and a glass-like protective layer is formed on the first surface. The membrane is clamped between the front plate and the back plate. The first surface of the membrane is in contact with the front plate and the glass-like protective layer is exposed toward outside of the sample holder through the opening of the front plate. The second surface of the membrane connects to the groove of the back plate. After gaps between the front plate and the membrane and between the membrane and the back plate are vacuum sealed, the liquid is injected into the groove and then the inlet is vacuum sealed so that the liquid is in contact with the second surface of the membrane to have the membrane in a wet condition. The material of the front plate and the back plate can be separately of metal, alloy, or plastics.

In addition, the membrane can be, for example, an asymmetric membrane or have a multilayered structure.

In a second embodiment of the present invention, a sample holder suitable to be used in measuring the characteristic of a membrane in a wet condition by a positron annihilation spectrometer is disclosed. The sample holder comprises a front plate and a back plate. The front plate has an opening and the back plate comprises a groove and an inlet where the inlet connects to the groove. The membrane has a first surface and a second surface opposing to the first surface and a glass-like protective layer is formed on the first surface. The membrane is clamped between the front plate and the back plate. The first surface of the membrane is in contact with the front plate and the glass-like protective layer is exposed toward the outside of the holder through the opening of the front plate. The second surface of the membrane connects to the groove of the back plate. After gaps between the front plate and the membrane and between the membrane and the back plate are vacuum sealed, a liquid is injected into the groove and then the inlet is vacuum sealed so that the liquid is in contact with the second surface of the membrane to have the membrane in a wet condition. The glass-like protective layer can be a deposition layer comprising silicon, oxygen, carbon, and hydrogen formed on the first surface of the membrane by a plasma enhanced chemical vapor deposition method or any other method. Besides, the thickness of the glass-like protective layer is 650 nm~5000 nm to have a property of vacuum sealing that the liquid can not permeate into the vacuum chamber through the glass-like protective layer and preferably around 700 nm~1500 nm. If the glass-like protective layer were too thick, it is unfavorable for the positron beam to impact the membrane during measurement. On the contrary, if the glass-like protective layer were too thin, the glass-like protective layer may not be able to prevent air from permeating into the vacuum chamber through the glass-like protective layer. The above "vacuum seal" means that gas cannot pass through. Gaps between the front plate and the membrane and between the membrane and the back plate are vacuum sealed by a vacuum sealant so that gas can not pass through the inlet.

In a third embodiment of the present invention, a sample holder suitable to be used in measuring the characteristics of at least one membrane in a wet condition by a positron annihilation spectrometer is further disclosed. Compared to the second embodiment, the sample holder according to the third embodiment can be used to mount a plurality of membranes at the same time. By providing the sample holder on a motion feedthrough, the relations of various sets of the membrane and the liquid or individual membrane can be studied efficiently.

According to the third embodiment of the invention, the sample holder comprises a front plate and a back plate. The front plate has at least one opening and the back plate comprises at least one groove and at least one inlet where each groove corresponds to one inlet of the back plate and one opening of the front plate and the numbers of openings, grooves, inlets are the same. Each membrane has a first surface and a second surface opposing to the first surface and a glass-like protective layer is formed on the first surface of each membrane. Each membrane is clamped between the front plate and the back plate. The first surface of each membrane is in contact with the front plate and the glass-like protective layer is exposed toward outside of the holder through the corresponding opening of the front plate. The second surface of each membrane connects to the corresponding groove of the back plate. After gaps between the front plate and each membrane and between each membrane and the back plate are vacuum sealed, at least one liquid is injected into at least one groove to have the corresponding membrane in a wet condition and then the corresponding inlet is vacuum sealed. The glass-like protective layer can be a deposition layer comprising silicon, oxygen, carbon, and hydrogen formed on the first surface of the membrane by a plasma enhanced chemical vapor deposition method or any other method. Besides, the thickness of the glass-like protective layer is 650 nm~5000 nm to have a property of vacuum sealing that the liquid can not permeate into the vacuum chamber through the glass-like protective layer and preferably around 700 nm~1500 nm. If the glass-like protective layer were too thick, it is unfavorable for the positron beam to impact the membrane during measurement. On the contrary, if the glass-like protective layer were too thin, the glass-like protective layer may not be able to prevent air from permeating into the vacuum chamber through the glass-like protective layer. The above "vacuum seal" means that gas cannot pass through. Gaps between the front plate and the membrane and between the membrane and the back plate are vacuum sealed by a vacuum sealant so that gas can not pass through the inlet.

The following will describe the invention in details by examples but the scope of the invention is not limited to these examples.

At first, an AETH-TMC/mPAN composite membrane is to be prepared. 2-aminoethanethiol (AETH) and trimesoyl chloride (TMC) are reacted to carry out the interfacial polymerization on the surface of a modified polyacrylonitrile (mPAN) asymmetric membrane to form an active layer of poly(thiol ester amide). Thus, the AETH-TMC/mPAN composite membrane is obtained. Then, a plasma polymerization procedure on the AETH-TMC/mPAN composite membrane is performed to form a glass-like protective layer ($SiO_xC_yH_z$ layer where x, y, and z indicate the composition ratios) on one surface of the AETH-TMC/mPAN composite membrane. That is, the plasma enhanced chemical vapor deposition (PECVD) is carried out. After the reactor is evacuated down to a pressure of $10^{-2}$ torr, the process pressure is adjusted to about 0.2 torr and the temperature is set at 25° C., the plasma power is applied at 150 W, and the flow rate of the TEOS (tetrathoxysilane) monomer is controlled at 12.4 mg/min. Thus, the $SiO_xC_yH_z$/AETH-TMC/mPAN composite membrane is obtained as a composite membrane to be characterized. The $SiO_xC_yH_z$/AETH-TMC/mPAN composite membrane is mounted on the sample holder according to the invention. After injection of IPA (iso-propyl alcohol), the inlet of the sample holder is vacuum sealed and the PAS measurement is performed. In another example, the IPA/$H_2O$ solution or water ($H_2O$) is injected.

Figure 2:
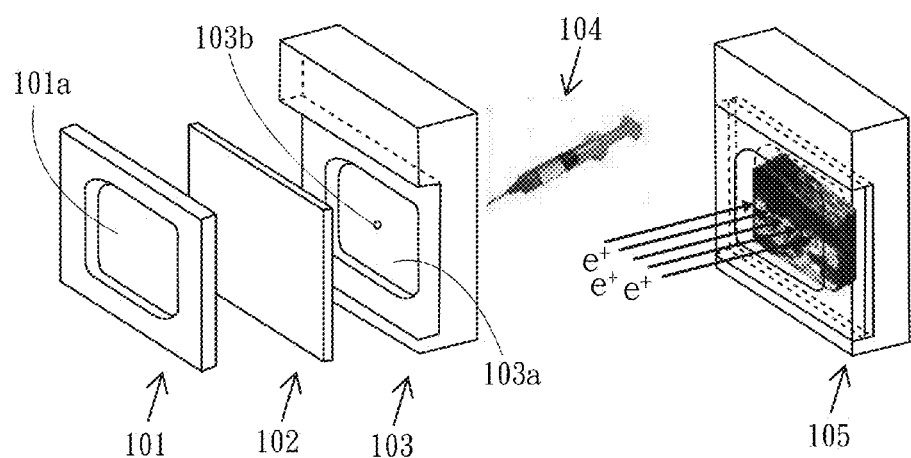
FIG. 2 shows an explosive schematic diagram and an assembled schematic diagram illustrating the sample holder and the composite membrane according to one embodiment of the present invention.
Figure 3:
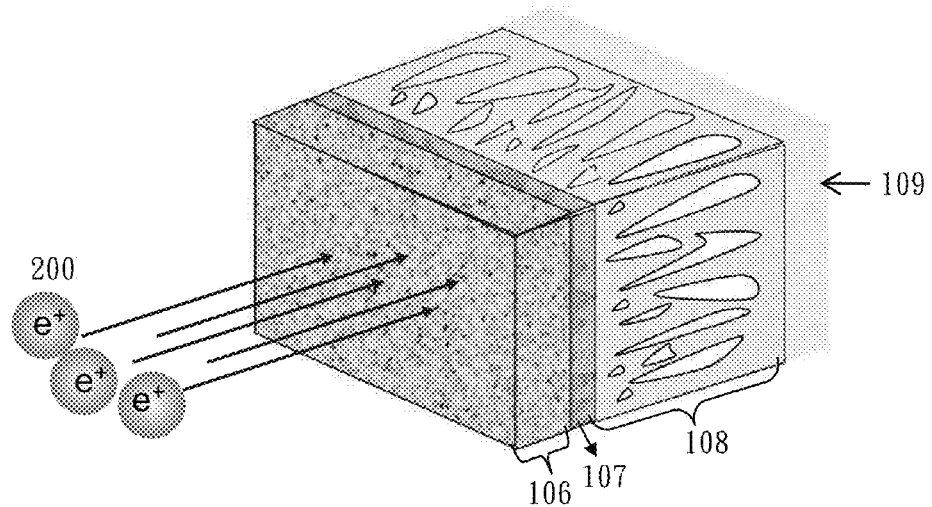
FIG. 3 shows an enlarged schematic diagram illustrating the multilayered structure of the composite membrane according to one embodiment of the present invention.

Please refer to FIGS. 1~3. FIG. 1 shows a schematic diagram of a positron annihilation spectrometer 10 where 100 indicates a sample holder according to the invention. FIG. 2 shows an explosive schematic diagram (on the left hand side) and an assembled schematic diagram (on the right hand side) illustrating the sample holder and the composite membrane according to one embodiment of the present invention where 101 indicates a front plate, 102 indicates a composite membrane, 103 indicates a back plate, 103a indicates the groove on the back plate 103, 103b indicates the inlet on the back plate 103, 104 indicates the injection syringe for injecting liquids or solutions, 105 indicates the assembled sample holder by using epoxy glue to assemble the front plate, the membrane, and the back plate together and to vacuum seal the gaps among them. FIG. 3 shows an enlarged schematic diagram illustrating the multilayered structure of the composite membrane according to one embodiment of the present invention where 106 is the $SiO_xC_yH_z$ layer, 107 is the AETH-TMC layer, 108 is the mPAN layer, 109 is the solution, and 200 is the positron beams (variable monoenergy slow positron beam; VMSPB). In this example, the variable monoenergy slow positron beam (VMSPB) is used, 50 mCi of $^{22}$Na is used as the positron source, and two positron annihilation spectrometers are connected to the beam, namely Doppler broadening energy spectroscope (DBES) and positron annihilation lifetie spectroscope (PALS) which use the secondary electrons emitted from the sample surface as a starting signal.

Figure 4:
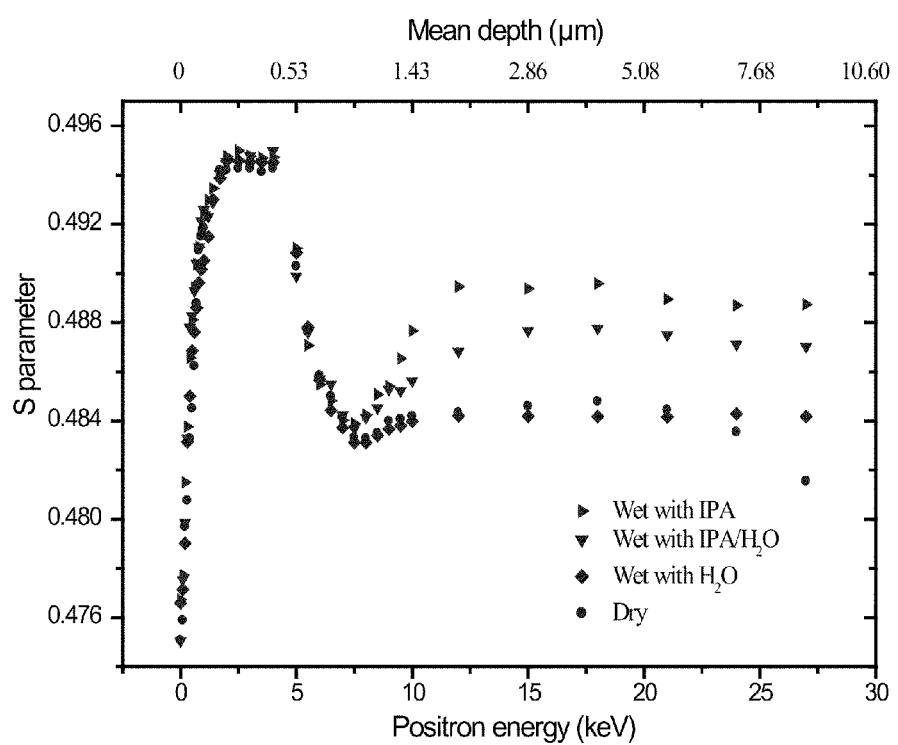
FIG. 4 shows the relation of S parameter and the positron incident energy or mean depth in dry and wet states of $SiO_x$-$C_yH_z$/AETH-TMC/mPAN composite membranes according to one embodiment of the present invention where solvents used to keep membrane wet are: IPA (iso-propyl alcohol), 70 wt % $IPA/H_2O$, and $H_2O$.

The following will describe the swelling behavior influence on the free volume of the $SiO_xC_yH_z$/AETH-TMC/mPAN composite membrane. Experiments on positron annihilation spectroscopy (PAS) coupled with a VMSPB were performed as a function of positron energy form 100 eV to 30 keV in both dry and the wet $SiO_xC_yH_z$/AETH-TMC/mPAN composite membrane. Both Doppler Broadening Energy Spectra (DBES) and Positron Annihilation Lifetime Spectra (PALS) were measured to obtain the depth profiles and the free volume information. FIG. 4 shows the relation of S parameter and the positron incident energy or mean depth in dry and wet states of $SiO_xC_yH_z$/AETH-TMC/mPAN composite membranes according to one embodiment of the present invention where solvents used to keep membrane wet are: IPA (iso-propyl alcohol), 70 wt % IPA/$H_2O$, and $H_2O$. The variation in the S parameter reveals the variation in the free volumes and the multilayered structures in asymmetric polymeric materials and membranes.

Figure 5:
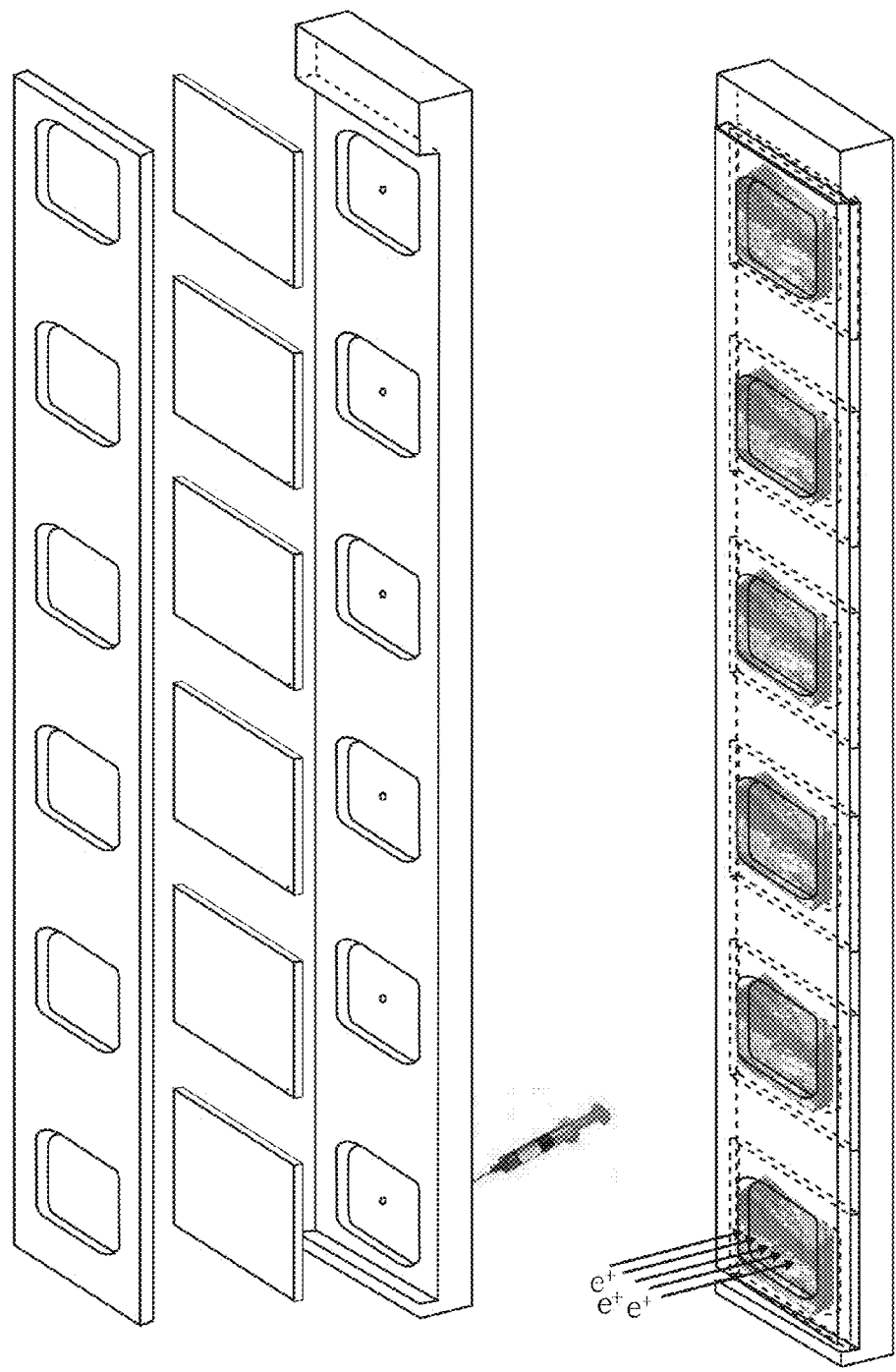
FIG. 5 shows an explosive schematic diagram and an assembled schematic diagram illustrating the sample holder and the composite membrane according to another embodiment of the present invention.

Furthermore, FIG. 5 shows an explosive schematic diagram and an assembled schematic diagram illustrating the sample holder and the composite membrane according to another embodiment of the present invention. As shown in FIG. 5, the sample holder can be used to mount a plurality of membranes at the same time. By providing the sample holder on a motion feedthrough, the relations of various sets of the membrane and the liquid or individual membrane can be studied efficiently. Besides, the sample holder according to the invention can be provided on various stages (motion stage or rotation stage) or various vacuum systems to carry out a wide variety of tests and measurements.

Obviously many modifications and variations are possible in light of the above teachings. It is therefore to be understood that within the scope of the appended claims the present invention can be practiced otherwise than as specifically described herein. For example, the shape of the sample holder is not necessarily rectangular shown in FIG. 2 and can be other shape like circular or polygonal. The shape of the opening of the front plate of the sample holder is not necessarily circular shown in FIG. 2 and can be other shape. Although specific embodiments have been illustrated and described herein, it is obvious to those skilled in the art that many modifications of the present invention may be made without departing from what is intended to be limited solely by the appended claims.

What is claimed is:

1. A method for characterizing a membrane in a wet condition by a positron annihilation spectrometer, comprising:
    providing a membrane to be characterized wherein the membrane has a first surface and a second surface opposing to the first surface;
    performing a plasma polymerization procedure on the first surface of the membrane to form a glass-like protective layer;
    mounting the membrane formed with the glass-like protective layer on a sample holder to have the first surface of the membrane exposed and the second surface vacuum sealed in the sample holder;
    injecting a liquid into the sample holder through an inlet on the sample holder to have the liquid be in contact with the second surface of the membrane;
    sealing the inlet and then placing the sample holder into the vacuum chamber of the positron annihilation spectrometer; and
    having a positron beam impact the glass-like protective layer to thereby characterize the membrane and obtain the characteristic(s) of the membrane;
    wherein the glass-like protective layer has a property of vacuum sealing that the liquid can not permeate into the vacuum chamber through the glass-like protective layer.

2. The method according to claim 1, wherein the plasma polymerization procedure is to use a plasma enhanced chemical vapor deposition method to form a glass-like protective layer comprising silicon, oxygen, carbon, and hydrogen on the first surface of the membrane.

3. The method according to claim 1, wherein the glass-like protective layer is a deposition layer comprising silicon, oxygen, carbon, and hydrogen.

4. The method according to claim 1, wherein the step of sealing the inlet is to seal the inlet by a vacuum sealant to prevent air from passing through the inlet.

5. The method according to claim 1, wherein the characteristic(s) of the membrane obtained from the method are the free volumes or layer structures of the membrane.

6. The method according to claim 1, wherein the thickness of the glass-like protective layer is around 650~5000 nm.

7. The method according to claim 1, wherein the thickness of the glass-like protective layer is around 700~1500 nm.

8. The method according to claim 1, wherein the sample holder comprises:
    a front plate, having an opening; and
    a back plate, comprising a groove and an inlet wherein the inlet connects to the groove;
    wherein the membrane is clamped between the front plate and the back plate;

the first surface of the membrane is in contact with the front plate and the glass-like protective layer is exposed toward outside of the holder through the opening of the front plate;

the second surface of the membrane connects to the groove of the back plate; and after gaps between the front plate and the membrane and between the membrane and the back plate are vacuum sealed, the liquid is injected into the groove and then the inlet is vacuum sealed so that the liquid is in contact with the second surface of the membrane to have the membrane in a wet condition.

9. The method according to claim 1, wherein the membrane is an asymmetric membrane or has a multilayered structure.

10. The method according to claim 8, wherein the material of the front plate and the back plate is separately of metal, alloy, or plastics.

11. A sample holder, suitable to be used in measuring the characteristic of a membrane in a wet condition by a positron annihilation spectrometer, the sample holder comprising:

a front plate, having an opening; and a back plate, comprising a groove and an inlet wherein the inlet connects to the groove;

wherein the membrane has a first surface and a second surface opposing to the first surface and a glass-like protective layer is formed on the first surface;

the membrane is clamped between the front plate and the back plate;

the first surface of the membrane is in contact with the front plate and the glass-like protective layer is exposed toward outside of the holder through the opening of the front plate;

the second surface of the membrane connects to the groove of the back plate; and after gaps between the front plate and the membrane and between the membrane and the back plate are vacuum sealed, a liquid is injected into the groove and then the inlet is vacuum sealed so that the liquid is in contact with the second surface of the membrane to have the membrane in a wet condition.

12. The sample holder according to claim 11, wherein the glass-like protective layer is a deposition layer comprising silicon, oxygen, carbon, and hydrogen.

13. The sample holder according to claim 11, wherein the glass-like protective layer is formed by a plasma enhanced chemical vapor deposition method and comprises silicon, oxygen, carbon, and hydrogen.

14. The sample holder according to claim 11, wherein the thickness of the glass-like protective layer is around 650~5000 nm.

15. The sample holder according to claim 11, wherein the thickness of the glass-like protective layer is around 700~1500 nm.

16. The sample holder according to claim 11, wherein gaps between the front plate and the membrane and between the membrane and the back plate are vacuum sealed by a vacuum sealant so that gas can not pass through the inlet.

17. A sample holder, suitable to be used in measuring the characteristics of at least one membrane in a wet condition by a positron annihilation spectrometer, the sample holder comprising:

a front plate, having at least one opening; and a back plate, comprising at least one groove and at least one inlet wherein each groove corresponds to one inlet of the back plate and one opening of the front plate and the numbers of openings, grooves, inlets are the same;

wherein each membrane has a first surface and a second surface opposing to the first surface and a glass-like protective layer is formed on the first surface of each membrane;

each membrane is clamped between the front plate and the back plate;

the first surface of each membrane is in contact with the front plate and the glass-like protective layer is exposed toward outside of the sample holder through the corresponding opening of the front plate;

the second surface of each membrane connects to the corresponding groove of the back plate; and after gaps between the front plate and each membrane and between each membrane and the back plate are vacuum sealed, at least one liquid is injected into at least one groove to have the corresponding membrane in a wet condition and then the corresponding inlet is vacuum sealed.

18. The sample holder according to claim 17, wherein the glass-like protective layer is a deposition layer comprising silicon, oxygen, carbon, and hydrogen.

19. The sample holder according to claim 17, wherein the glass-like protective layer is formed by a plasma enhanced chemical vapor deposition method and comprises silicon, oxygen, carbon, and hydrogen.

20. The sample holder according to claim 17, wherein the thickness of the glass-like protective layer is around 700~1500 nm.

* * * * *